United States Patent [19]
Carr

[11] Patent Number: 5,906,487
[45] Date of Patent: May 25, 1999

[54] MIRROR ASSEMBLY FOR USE IN ENDODONTIC PROCEDURES

[76] Inventor: Gary B. Carr, 5035 El Acebo, P.O. Box 1831, Rancho Santa Fe, Calif. 92067

[21] Appl. No.: 09/032,499

[22] Filed: Feb. 26, 1998

[51] Int. Cl.⁶ .................................................. A61B 1/24
[52] U.S. Cl. ................................... 433/30; 359/838
[58] Field of Search ................. 433/30, 31; 359/838, 359/871, 872, 882, 883, 884

[56] References Cited

U.S. PATENT DOCUMENTS

| 5,042,887 | 8/1991 | Yamada | 359/360 |
| 5,269,683 | 12/1993 | Hickok et al. | 433/30 |
| 5,507,175 | 4/1996 | Cooper | 73/29.02 |

*Primary Examiner*—John J. Wilson
*Attorney, Agent, or Firm*—Wood, Herron & Evans, LLP

[57] ABSTRACT

A mirror assembly adaptable for use in conjunction with a microscope comprises a sapphire substrate having an outer surface for forming a damage-resistant first surface, and an inner surface with a layer of reflective material adhered to the inner surface of the sapphire substrate for providing a reflective second surface to produce a mirror optical image. The sapphire substrate provides support and protection for the reflective material layer and reflective second surface, whereby a bright, single, mirror optical image is provided for microscopic magnification.

25 Claims, 1 Drawing Sheet

U.S. Patent  May 25, 1999  5,906,487
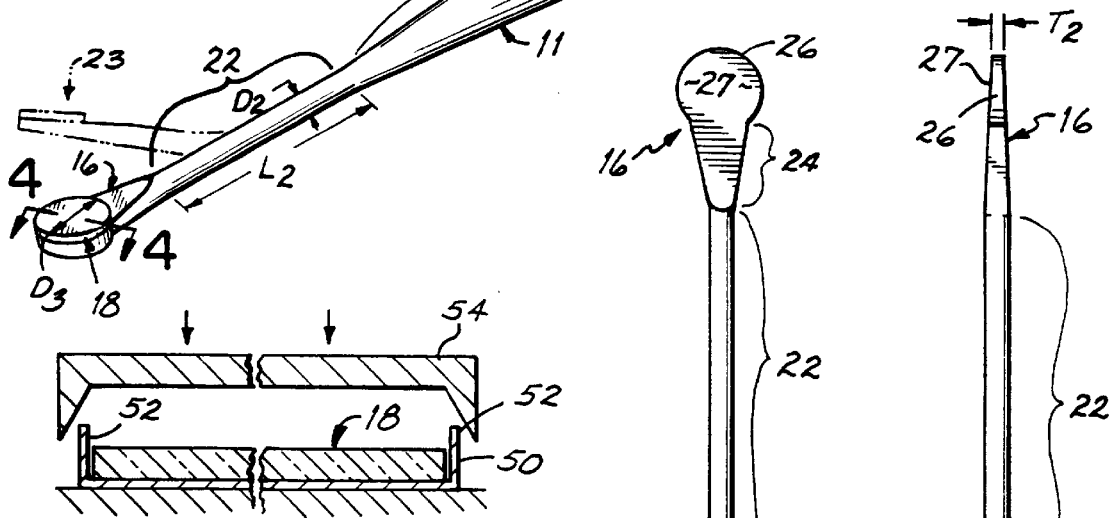
FIG. 1
FIG. 5
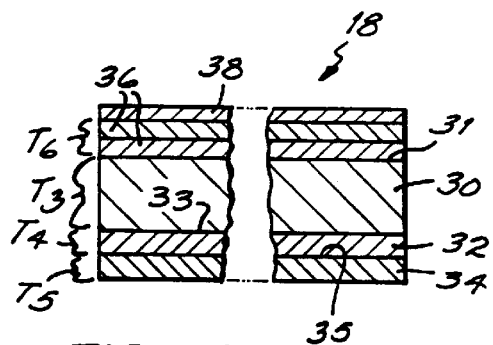
FIG. 4
FIG. 5A
FIG. 2
FIG. 3

MIRROR ASSEMBLY FOR USE IN ENDODONTIC PROCEDURES

FIELD OF THE INVENTION

This invention relates to microscopic endodontic surgery, and more specifically to a mirror device for providing reflective images of dental tissue to a microscope during such endodontic procedures.

BACKGROUND OF THE INVENTION

The use of hand mirrors for examining inside the mouth during dental procedures is well known. Traditionally, most mirrors were utilized to examine the interior of the mouth and the exterior surfaces of the teeth. As such, they were large enough to provide the dentist or oral surgeon with an image which could be viewed with the naked eye. Endodontic procedures, however, involve work on the interior of a tooth within very small spaces and thus have produced the need for a substantially smaller mirror surface for providing an image of the interior dental tissue or root of the tooth.

During endodontic surgical procedures, such as retrofilling preparations on the inner end or tip of a tooth root, a small opening or aperture is formed, generally through the jaw bone and the tissue surrounding a tooth, to provide exposure of the dental root. To form the apertures for working on the tooth root, very small drills are utilized so that the required interior work space will be very small. The surgical work is performed using a surgical microscope to view the tooth root in the small work space that is created by drilling through the jaw proximate the tooth root. An endodontic mirror is used to provide a reflected optical image, and the microscope then magnifies the reflected optical image provided by the endodontic mirror for viewing by the surgeon. Because of the small work space, the endodontic mirror must be very small, but still must be capable of providing a bright, distortion-free optical image for magnification by the microscope.

Endodontic mirrors are available for such applications, as evidenced by U.S. Pat. No. 5,269,683, issued to Hickok et al. While the Hickok et al. mirror is suitable for providing a useful optical image, it has a variety of drawbacks which affect the quality of the optical image provided and thus affect the overall endodontic procedure. First, the mirror is a single surface mirror which has an exposed reflective surface of polished tungsten-carbide. The tungsten-carbide has been found to absorb a significant amount of visible light, thus reflecting an optical image of reduced brightness to the microscope. Endodontic surgical microscopes, however, require a large amount of light for work in the small, dark spaces of the interior of the jaw proximate a tooth root. Low light conditions and a darkened optical image during an endodontic microsurgical procedure are not only annoying to the surgeon, but also may affect the surgeon's ability to perform the procedure efficiently and properly.

An additional drawback to available endodontic mirrors is their susceptibility to damage by other endodontic instruments used during a microsurgical procedure inside the mouth. The mirrors are usually what are referred to as "first surface mirrors," and their reflective surface is exposed. Therefore, the reflective surface is easily scratched by irrigator tips and probes which are generally made out of stainless steel. Therefore, great care must be taken during the endodontic procedure to avoid contacting the exposed reflective surface with other, harder instruments. However, contact is often unavoidable and damage results. A damaged reflective mirror surface further degrades the optical image provided to the microscope.

One way to reduce such damage to the reflective surface is to provide a protective surface or layer on top of the reflective surface to thus create what is referred to as a "second surface" mirror. However, second surface mirrors have traditionally been subject to double imaging or "ghost" imaging. Light reflects from not only the second reflective surface, but also from the first protective surface, and thus provides second or ghost images of the area of interest. Ghost images are very undesirable in microscopic endodontic surgery wherein it is oftentimes difficult to obtain a suitable single optical image. The microscope magnifies these double images and makes detailed examination of the root end difficult.

Another drawback to existing endodontic mirrors is that they are susceptible to chemical and heat damage. Endodontic implements must be sterilized between uses. Usually a high temperature autoclave (~200° C.) is used to heat the implements for sterilization. The reflective surface of first surface mirrors may be subject to warpage and other temperature-induced damage during autoclaving. Furthermore, aggressive chemicals utilized in chemical sterilization procedures degrade the optical surface. Still further, weak acids often present in the mouth can adversely affect an endodontic mirror's reflectivity.

Available endodontic mirrors have also been relatively expensive and generally are not made for use with universal dental handles. Each mirror is machined with its own dedicated handle which creates a substantial expense for the endodontic surgeon, who will generally require a number of endodontic mirrors having different sizes and shapes.

Accordingly, it is an object of the present invention to provide a highly reflective endodontic mirror which provides a bright optical image for microscopic surgical procedures.

It is another objective of the present invention to provide a mirror which is durable and damage resistant, and which may be manipulated with other surgical instruments in an endodontic procedure without degrading the reflective surface.

It is still another objective of the present invention to provide a clear, usable optical image without double imaging or ghost imaging.

It is another objective to provide an endodontic mirror which is relatively inexpensive and suitable for use with existing dental equipment such as universal dental handles.

It is still another objective of the present invention to provide an endodontic mirror which is highly resistant to repeated sterilization and exposure to chemical solutions which are encountered during endodontic procedures.

SUMMARY OF THE INVENTION

The inventive mirror device addresses the drawbacks of the prior art and provides a durable, highly reflective endodontic mirror in accordance with the objectives set forth hereinabove. The mirror provides bright, clear and single-image optical images which may be suitably magnified by a microscope.

The mirror blank of the inventive mirror device comprises a single crystal, optical-grade sapphire substrate, the back or inner surface of which is provided, in one embodiment, with a pure aluminum or silver reflective layer. In another embodiment, a dielectric white light reflective coating may be used. The sapphire substrate provides a hard protective layer for the reflective surface, and is optically clear with no surface or internal distortions. It has been found that the sapphire substrate provides an 85–90% light transmission for light within the visible range. The sapphire prevents heat and chemical damage to the reflective surface and provides a virtually indestructible mirror with very good reflective qualities to provide a bright optical image suitable for microscopic magnification. The hard sapphire substrate prevents damage to the reflective surface by other endodontic instruments, such as probes or irrigator tips.

The pure aluminum or silver reflective surface of one embodiment of the inventive mirror, that is, the second surface, is deposited in situ by vacuum vapor deposition. The aluminum, by reason of being deposited in a vacuum, is not exposed to oxygen and has an approximately 90%±=5% reflection rate of the visible light spectrum which is transmitted through the protective sapphire substrate layer. The mirror provides a bright optical image since aluminum is one of the best reflective surfaces available. The sapphire substrate provides protection to the aluminum reflective surface to make the mirror virtually impervious to damage by other endodontic instruments, chemicals, etc.

To further reduce scratching and damage to the aluminum reflective surface, a durable protective film is deposited on the exposed, or back side, of the aluminum reflective surface which functions as a protective layer. The protective layer may be a protective oxide coating, such as silicon monoxide which is deposited in situ by vacuum vapor deposition. Alternatively, an organic coating or fluoropolymer coating, such as Teflon™, might also be utilized.

The inventive mirror device further comprises anti-glare or anti-reflective coatings which are deposited on the outer or exposed surface of the sapphire substrate opposite the inner surface containing the reflective surface. The surface of the sapphire substrate on which the anti-glare coatings are deposited are considered the "first surface" of the mirror because it is the surface first encountered by the light from the dental surface being viewed. The "second surface" of the mirror is the inner surface of the sapphire substrate opposite the outer surface thereof which constitutes the first surface of the mirror. The anti-glare coating is preferably formed of several layers which are vacuum deposited on the sapphire and create a first surface reflectance which is less than 0.5% for light in the range of 435–670 nanometers at a 0° incident angle relative to the first surface of the sapphire substrate. The anti-glare coating layers reduce glare and ghost images from first surface reflections by absorbing or dissipating any light reflected from the first surface of the sapphire substrate, a phenomenon called "total internal reflection." The mirror device thus provides a clearer and sharper image on the optical substrate. Thus, the inventive mirror does not provide a ghost optical image to the microscope. The anti-glare coatings, which may be, for example, compositions of $ZrO_2/MgO_2$ or $HfO_2/NgO_2$, are also resistant to organic solvents, endodontic chemicals, water, and the weak acids which are found in the mouth.

To provide further protection for the mirror, a protective coating or layer may be placed on the anti-glare coatings, similar to the protective coating utilized to protect the reflective coating or layer.

The inventive mirror is supported on one end of a stem or a mirror foot which is flexible for particular applications within an endodontic procedure. The stem is preferably formed of 300 series stainless steel, such as 316-L (low carbon) stainless steel, which is ductile and not particularly brittle. The stem is machined from stainless steel rod stock and includes a collet shank which is formed on the end of the stem opposite that which is connected to the mirror blank. The collet shank is preferably formed for insertion into standard, universal dental handles, and may include a blade design, a rod design, or a male/female threaded end design. In one preferred embodiment of the invention, a flat blade is utilized for interfacing with a standard dental collet.

From the collet shank, the stem has a circular cross section and is tapered to enhance flexibility. The tapered section tapers down to a flexible or bendable stem section which maintains a consistent or non-tapering diameter out to the mirror foot which supports the mirror blank. The untapering section is bendable to provide adjustment of the angle of the mirror foot and attached mirror blank. The mirror blank may be attached to the foot with an autoclavable FDA-approved adhesive. Alternatively, the mirror blank is held in a stainless steel cup by crimping the cup around the blank. The cup is then secured to the foot, such as by spot welding. The untapering, bendable section may be plastically deformed with a force of approximately 2–6 Newtons.

The stem then flares to or tapers outwardly to provide a symmetrically beveled mirror foot. The flare of the stem in transition to the mirror foot insures increased rigidity at the interface of the mirror foot and the bendable section. The symmetrically beveled mirror foot provides a thin, flat area, which is configured to support the mirror blank. The mirror blank, and thus the mirror foot can take any number of different shapes, such as circular, elliptical, rectangular and/or square. The stem is machined from stainless steel rod stock having an O.D. of approximately 3.5 millimeters. After machining, the stainless steel is annealed at approximately 1200° C. to provide good ductility to the stem and particularly to the non-tapering bendable section.

The inventive mirror assembly is thus durable and damage resistant, and provides a bright, clear optical image for microscopic magnification. The bright image provides a better view for the surgeon, and the reduced ghost imaging provides a clear optical image which may be magnified without distortion. The collet shank provides interfacing with a variety of different available dental handles and thus, the cost of the mirror may be reduced by eliminating the need for a dedicated handle.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

FIG. 1 is a perspective view of the inventive mirror assembly with a blade-type collet shank for interfacing with a universal dental handle.

FIG. 2 is a top view of the endodontic mirror device.

FIG. 3 is a side view of the endodontic mirror device.

FIG. 4 is a partial cross-sectional view of the various layers of the mirror blank used with the inventive mirror device.

FIG. 5 is a cross-sectional view of an alternative embodiment of the invention.

FIG. 5A is a cross-sectional view of the embodiment of FIG. 5 showing the cup crimped.

DETAILED DESCRIPTION OF THE INVENTION

Referring to FIG. 1, the endodontic mirror device 10 of the invention, includes a stainless steel stem 11 having a collet shank 12, a tapering section 14, a flexible or bendable section 22 and a mirror foot 16, which supports a reflective mirror blank 18. The shank 12, tapering 14 and bendable 22 sections and mirror foot 16 are all preferably formed from a single piece of 300 series stainless steel rod stock. Preferably, 316-L stainless steel is utilized because of its low carbon content and its ductility and very low brittleness. In a preferred embodiment of the invention, the rod stock has a diameter $D_1$, of approximately 3.50 millimeters (see FIG. 3). The overall length of the stock for one preferred embodiment is approximately 49.5 millimeters. It will be understood by a person of ordinary skill in the art, however, that different dimensions might be utilized. The rod is turned on a computer-controlled lathe for producing the necessary tapered flexible and non-tapered sections, as discussed further hereinbelow. The collet shank 12 and mirror foot 16 are then ground or milled to provide flat surface sections as shown in FIG. 1 and 3.

The collet shank 12 in the disclosed embodiment, is blade-shaped and has a width $W_1$ of approximately 3.5 mm, or the largest diameter of the bar stock. The collet shank in the disclosed embodiment has a length $L_1$ which is approximately 13 mm including a tapered region 19 where the flat collet shank interfaces with the circular cross section of the stem 11. The blade-shaped collet shank 12 is milled flat to have a thickness $T_1$. of approximately 0.7 mm (see FIG. 3). The collet shank 12 is shown as a blade. However, a rod design, or a male/female threaded design might be utilized for interfacing with standard, universal dental handles having appropriately shaped shank-receiving ends. The collet shank blade 12 illustrated is designed to interface with a standard dental collet (0.7 mm×10.5 mm). However, the shank 12 could also be sized to fit with collets of other sizes.

The stem 11 includes the tapering region 14 of circular crosssection which tapers down from the maximum diameter (i.e. 3.5 mm) to form the flexible or bendable section 22 directly adjacent the mirror foot 16. The flexible section 22 is approximately 10 mm in length $L_2$ and is also circular in cross-section having a diameter $D_2$ of approximately 0.7 mm. The bendable section 22 does not taper, but has a uniform diameter $D_2$ throughout its length and may be bent at an angle to the rest of the stem 14 to provide for adjustment of the angle of mirror foot 16 and mirror blank 18 Section 22 may preferably be bent or plastically deformed with a force of approximately 2–6 Newtons, or approximately 1 lb. Therefore, very little force is needed to adjust the angle of mirror blank 18 for a particular endodontic procedure. Bendable section 22 is resilient and ductile and may be bent and adjusted repeatedly to change the mirror angle as necessary and as shown in phantom 23 in FIG. 1.

In another embodiment of the invention, stem 11 might be formed from a Nickel-Titanium (Ni-Ti) material such as material available from Shape Memory Applications in San Jose, California. Ni-Ti material has a shape memory which is set at a very high temperature. At or below a low temperature threshold, the material is flexible and bendable and will retain the bent shape as long as the temperature of the material remains below the low temperature threshold. By heating the material above the low threshold temperature, but still substantially below the temperature at which the memory is set, the material will return to its original, set shape. No kinks remain in the material when it is heated back to its original shape. Therefore, the Ni-Ti material may be used repeatedly without work hardening and thus has a longer useful life. Such a material is particularly suitable for the stem of the inventive mirror device since it will be repeatedly bent in different endodontic procedures to different shapes to adjust the angle of the mirror blank as required for each procedure.

Mirror device 10 and specifically stem 11 is preferably machined and then subsequently annealed to provide for better ductility. 300 series stainless steel is a good material for machining; however, it is more rigid than desired for the adjustable mirror of the invention. Accordingly, after the rod stock has been completely machined it is annealed by placing it within an annealing oven at 1200° C. The machined piece is placed in the oven at room temperature and the oven temperature is rapidly raised to 1200° C. The stem 11 is then immediately removed to be cooled at room temperature. The annealing improves the ductility of the stainless steel and thus provides for the proper consistency for the bendable section 22. The length of time of the annealing will depend upon the thickness of the rod stock in accordance with well-known annealing procedures.

Referring to FIG. 2, the mirror foot 16 includes a flared section 24 directly preceding a mirror base 26 for holding the mirror blank 18. The flared section 24 increases the rigidity of the stem 11 at the interface of the mirror foot 16 with bendable section 22 (See FIG. 2). Referring to FIG. 3, the mirror foot 16 is formed to provide a symmetrically beveled section having a flat surface 27 for mounting the mirror 18 on the mirror base 26. The shape of the mirror base 26 in the figures is shown as circular. However, different shapes might also be utilized such as elliptical, rectangular, and square, for handling those shapes of mirror blanks. In the embodiment disclosed in the figures, the mirror foot tapers down to a thickness $T_2$ of approximately 0.25 mm. Mirror blank 18 Is fixed to the flat surface 27 of the mirror base 26 utilizing FDA-approved, autoclavable adhesive, such as an adhesive available from Master Bond, Inc. as Part #EP42HTZ0005, or similar adhesive. Mirror blank 18 is secured after the annealing step discussed above.

Turning now to FIG. 4, which discloses a cross-section of the inventive mirror blank 18 utilized with the endodontic mirror device 10, a first layer 30, formed of a sapphire substrate, provides the durable base for the mirror blank 18. Sapphire substrate 30 is a single crystal, optical grade sapphire substrate which has few or no inclusions or faults, such as protrusions on surfaces thereof. A suitable optical grade sapphire is commercially available from companies such as Swiss Jewel Co. Sapphire substrate layer 30 is used primarily as a hard protective layer for an aluminum, silver, or dielectric white light reflective coating layer 32 which is deposited thereon. The sapphire layer 30 Is an optically clear sapphire with no surface or internal distortions, and preferably provides an 85–90% light transmission in the visible light range. The surfaces of the sapphire layer 30, including a first mirror surface 31, has a better than 40/20 scratch dig, as measured in the art. The first mirror surface is the outer surface of the sapphire layer 30. The durability of sapphire substrate layer 30 makes the inventive mirror blank 18 virtually indestructible and impervious to scratches from other endodontic implements and resistant to degradation by endodontic chemicals and mouth acids. The sapphire substrate utilized to make layer 30 has an average Young's Modulus of approximately 400 GPa, a Flexural Strength of approximately 900 MPa, and a hardness of 9 on the Moh's scale.

Referring to FIG. 4, in one embodiment of the present invention, sapphire substrate layer 30 has a thickness $T_3$ of approx imate ly 0.25 mm. For a circular shaped mirror 18 as illustrated in the figures, a diameter $D_3$ of approximately 3 mm would be suitable. For an elliptical shape (not shown), a length of 6 mm and a width of 3 mm might be suitable. It will be readily understood by a person of ordinary skill in the art, that endodontic mirrors must be very small for utilization in the small cavities or openings used in endodontic procedures.

The aluminum, silver, or dielectric white light reflective layer 32 provides the second mirror surface or reflective surface 33 for the mirror blank 18. Layer 32 may comprise a pure aluminum or silver film which is deposited in situ on the inner surface of the sapphire substrate by vacuum vapor deposition or other suitable deposition techniques. The aluminum preferably is not exposed to Oxygen during deposition to prevent oxidation, and has high reflectivity to reflect light in the visible spectrum as it is transmitted through the sapphire substrate. Pure aluminum is one of the best reflective surfaces available and in the inventive mirror blank 18, the second mirror surface 33 has an approximately 90% ±5% reflection of normal incident light. Silver is also a suitable reflective material in another embodiment. In an additional embodiment of the invention, a dielectric white light reflective surface could be used.

The sapphire layer 30 provides protection for the soft, damageable aluminum film, and provides a hard, but not brittle, layer which is able to withstand temperatures exceeding 1000° C. The combination of the sapphire layer 30 and reflective film layer 32 provides a mirror blank which generates very bright, clear images which can be magnified up to 40 times by a surgical microscope without significant distortion. Furthermore, the sapphire substrate layer 30 and reflective film layer 32 provides a mirror blank which is highly resistant to repeated sterilization and exposure to chemical solutions such as those solutions utilized during endodontic procedures, for example, root canal sterilization procedures. The mirror blank 18 is scratch resistant under severe surgical applications and thus its reflective properties will not be degraded through repeated use with other stainless steel implements such as probes and irrigator tips. The reflective film 32 will preferably have a thickness $T_4$ less than 4.0 microns.

To provide further protection for the reflective layer 32, which is very soft and easily damaged, a durable protective film or layer 34 is applied to the surface 35 of the layer 32 to protect layer 32. One such suitable protective film is clear silicon monoxide which is also suitable for vacuum vapor deposition on aluminum layer 32. Other durable films include non-organic coatings such as fluoropolymers including tetrafluoroethylene, marketed under the Teflon® trademark. A preferred thickness $T_5$ for protective layer 34 is 1.0 micron.

The sapphire substrate 30 in combination with the reflective layer 32, creates a "second-surface" mirror. In the past, second-surface endodontic mirrors and other second-surface mirrors have been susceptible to double imaging or ghost imaging, which is created by a reflection of light off the first surface 31 of the sapphire layer 30, as well as off of the second surface 33 of the reflective layer 32. That is, the original image is provided by reflection off of surface 33 while the ghost or secondary image appears from surface 31. The present invention utilizes one or more layers 36 of an anti-glare or anti-reflective coating. The anti-glare layers 36 are deposited upon the sapphire substrate, preferably by vacuum deposition. In the preferred embodiment of the invention, the anti-glare layers 36 reduce the reflectance from first-surface 31 to less than 0.5% of the visible light wavelength (approximately 435–670 nanometers) at a 0% or normal angle of incidence. Thus, the layers 36 of the anti-glare coating will absorb and dissipate reflections from first surface 31 to reduce glare and to reduce ghost images. Not only are the ghost images reduced, but a clearer and sharper image is provided to the reflective layer 32 to present a clear, reflected optical image which may be magnified up to 40 times by the surgical microscope without significant distortion.

Anti-glare coatings 36 are known in the photographic lens industry and suitable compositions for the anti-glare layers 36 are $ZrO_2/MgO_2$ or $HfO_2/MgO_2$ which are both frequently used for camera lenses. Layers 36 are preferably vacuum deposited onto the sapphire layer 30. Suitable anti-glare or anti-reflective coatings are very resistant to organic solvents, water, and the weak acids found in the mouth. Accordingly, the optical integrity of the combination sapphire/(alumninum or silver) mirror body is maintained. Preferably, the anti-glare layers have a cumulative thickness $T_6$ of between 2 and 4 Å, which will not significantly interfere with the passage of light to reflective layer 32.

To provide protection for the anti-glare layers 36 to prevent scratches or nicks thereto, another protective layer 38, similar in thickness and composition to layer 34, might be utilized.

The endodontic mirror device 10 of the invention is suitable for use with an autoclave for sterilization since the anti-glare layers 36 and protective coatings 34 and 38 will be deposited at temperatures substantially above 200° C. which is a typical temperature for autoclave sterilization. Furthermore, the protective layers 34 and 38 and the anti-glare layers 36 are resistant to endodontic chemical solutions and the acids of the mouth.

FIGS. 5 and 5A illustrate an alternative embodiment of the invention and, particularly, an alternative method of attaching the mirror blank 18 to the mirror base 26. Referring to FIG. 5, the blank 18 is inserted into a stainless steel cup 50. The depth of the cup 50 is such that an upper lip 52 extends above the blank 18. A crimping tool 54 is directed downwardly onto the cup to crimp lip 52 as illustrated. The annular crimped lip 52 captures the blank and holds it in the cup. The cup 50 is then adhered to the mirror base by an appropriate method, such as spot welding the cup to base 26.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details of representative apparatus and method, and illustrative examples shown and described. Accordingly, departures may be made from such details without departure from the spirit or scope of applicant's general inventive concept. For example, one preferred embodiment of the invention described herein lists certain shape, thickness, length, width, and diameter dimensions. However, it will readily be understood by a person of ordinary skill in the art that such dimensions might be varied according to the applications and/or dental handles used with the mirror device 10.

What is claimed is:

1. A mirror assembly adaptable for use in conjunction with a microscope comprising:

a support structure;

a light-transmissive sapphire substrate supported by the support structure and having an outer surface for forming a damage-resistant first surface, and an inner surface, the sapphire substrate arranged with respect to said support structure so as to have light incident on the first surface thereof pass through the substrate to said inner surface;

a layer of reflective material adhered to said inner surface of said sapphire substrate for providing a reflective second surface to light passing through the substrate to produce a mirror optical image, the sapphire substrate providing support and protection for said reflective material layer and reflective second surface;

whereby a bright, single, mirror optical image is provided for microscopic magnification.

2. The mirror assembly of claim 1 wherein said layer of reflective material includes one of aluminum, silver, and a dielectric white light reflective material.

3. The mirror assembly of claim 1 further comprising a protective layer adhered to said reflective material layer generally opposite said sapphire substrate for further protecting the reflective material layer.

4. The mirror assembly of claim 1 further comprising an anti-glare coating adhered to said sapphire substrate generally opposite said layer of reflective material, the anti-glare coating reducing reflections from said sapphire substrate to reduce multiple optical images from said mirror assembly.

5. The mirror assembly of claim 4 further comprising a protective layer adhered to said anti-glare coating generally opposite said sapphire substrate for protecting said anti-glare coating.

6. The mirror assembly of claim 4, wherein said anti-glare coating includes at least one of $HfO_2$, $MgO_2$ and $ZrO_2$.

7. The mirror assembly of claim 1, wherein said sapphire substrate is an optical grade sapphire.

8. The mirror assembly of claim 1, wherein said sapphire substrate is operable for transmitting at least approximately 80% of light incident thereon in the visible spectrum.

9. The mirror assembly of claim 1, wherein said sapphire substrate has a surface with at least 40/20 scratch dig.

10. The mirror assembly of claim 1, wherein said layer of reflective material provides at least approximately 90% reflection of visible light incident on said layer.

11. The mirror assembly of claim 1 wherein the support structure comprises a stem for supporting said sapphire substrate and said reflective material layer at an end thereof.

12. The mirror assembly of claim 11 wherein said stem includes a bendable section operable for being bent to vary the orientation of the sapphire substrate and reflective material layer relative to the end of the stem.

13. The mirror assembly of claim 11 wherein said stem includes a collet shank section at another end thereof for interfacing with a dental handle.

14. The mirror assembly of claim 11 wherein said stem is formed of 300 series stainless steel.

15. The mirror assembly of claim 14 wherein said stainless steel stem bas been annealed.

16. The mirror assembly of claim 1, wherein said support structure comprises a cup for holding said sapphire substrate.

17. The mirror assembly of claim 16 wherein said cup is formed of stainless steel.

18. A method of forming a mirror assembly for use in conjunction with a microscope comprising:

providing a support structure;

coupling to the support structure a light-transmissive sapphire substrate having an outer surface for forming a damage-resistant first surface and arranging the substrate with respect to the support structure so as to have light incident on the first surface thereof pass through the substrate;

applying a layer of reflective material to an inner surface of said sapphire substrate opposite the first surface for providing a reflective second surface to light passing through the substrate to produce a mirror optical image;

whereby the sapphire substrate provides support and protection for said reflective material layer and reflective second surface.

19. The method of claim 18 wherein said layer of reflective material is one of aluminum, silver, and a dielectric white light reflective material.

20. The method of claim 18 further comprising applying a protective layer to said reflective material layer generally opposite said sapphire substrate for further protecting the reflective material layer.

21. The method of claim 18 further comprising applying an anti-glare coating to said sapphire substrate generally opposite said layer of reflective material, the anti-glare coating reducing reflections from said sapphire substrate to reduce multiple optical images from said mirror assembly.

22. The method of claim 21 further comprising applying a protective layer to said anti-glare coating generally opposite said sapphire substrate for protecting said anti-glare coating.

23. The method of claim 21, wherein said anti-glare coating includes at least one of $HfO_2$, $MgO_2$ and $ZrO_2$.

24. The method of claim 18 further comprising coupling said sapphire substrate and said reflective material layer to a support structure including a stem which is adaptable for use with a dental tool.

25. The method of claim 24 wherein said stem includes a collet shank section at an end thereof for interfacing with a dental tool.

* * * * *